(12) United States Patent
Hart et al.

(10) Patent No.: US 7,081,128 B2
(45) Date of Patent: Jul. 25, 2006

(54) PHOTOTHERAPY DEVICE AND METHOD OF USE

(76) Inventors: Barry M. Hart, 8509 High Ridge Rd., Ellicott City, MD (US) 21043; Henryk Malak, 8444 High Ridge Rd., Ellicott City, MD (US) 21043

( * ) Notice: Subject to any disclaimer, the term of this patent is extended or adjusted under 35 U.S.C. 154(b) by 46 days.

(21) Appl. No.: 10/366,267

(22) Filed: Feb. 14, 2003

(65) Prior Publication Data
US 2003/0167080 A1   Sep. 4, 2003

Related U.S. Application Data

(60) Provisional application No. 60/361,161, filed on Mar. 4, 2002.

(51) Int. Cl.
*A61N 5/06* (2006.01)
(52) U.S. Cl. .......................... 607/89; 607/88
(58) Field of Classification Search ............ 606/9; 607/88–94; 128/898
See application file for complete search history.

(56) References Cited

U.S. PATENT DOCUMENTS

| | | | | |
|---|---|---|---|---|
| 4,029,085 A | * | 6/1977 | DeWitt et al. | 600/315 |
| 5,616,140 A | * | 4/1997 | Prescott | 606/10 |
| 6,045,575 A | * | 4/2000 | Rosen et al. | 607/88 |
| 6,290,713 B1 | * | 9/2001 | Russell | 607/88 |
| 6,443,978 B1 | * | 9/2002 | Zharov | 607/91 |
| 6,596,016 B1 | * | 7/2003 | Vreman et al. | 607/88 |
| 6,860,896 B1 | * | 3/2005 | Leber et al. | 607/1 |

* cited by examiner

*Primary Examiner*—Roy D. Gibson
*Assistant Examiner*—Henry M Johnson
(74) *Attorney, Agent, or Firm*—Armstrong, Kratz, Quintos, Hanson & Brooks, LLP

(57) ABSTRACT

A device is provided, in direct skin contact, surrounding an injured area for the treatment, reduction of joint inflammation, edema and excitation of neural and muscular stimulation associated with human and mammal tissues. This therapeutic light source includes a multiplicity of light emitting diodes (LED's) found in the ranges of 350 nm to 1000+ nm and fiber optic connections. A neoprene type material or other non-allergenic material is used to set the LED's and fiber optics in layers consisting of contact with the skin to few centimeters from the skin tissue. Distance will vary from contact or near contact with devices to several millimeters of separation. Each LED array is independently controlled allowing for optimal modulation of light frequencies and wavelengths. Technology is integrated allowing for biomedical feedback of tissue temperature and other statistical information. A low voltage, portable power supply, is integrated into the device as well as an analog/digital, input/output connection device. The design will be created for continuous wear, flexibility and comfort.

8 Claims, 4 Drawing Sheets
(1 of 4 Drawing Sheet(s) Filed in Color)

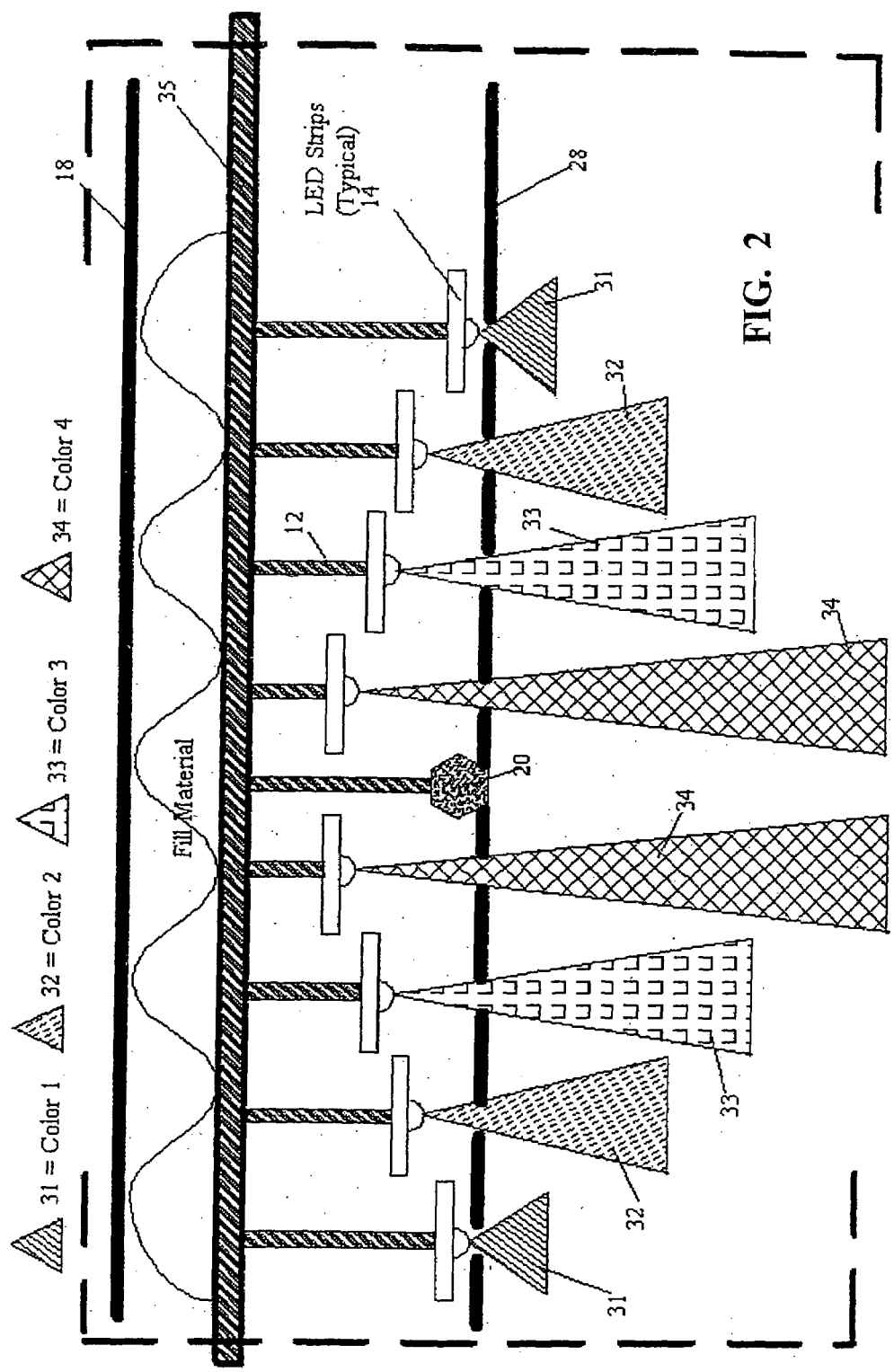

PHOTOTHERAPY DEVICE AND METHOD OF USE

RELATED APPLICATIONS

This application is claims benefit of Provisional Application No. 60/361,161 filed Mar. 4, 2002, which is herein incorporated by reference.

FIELD OF THE INVENTION

Design and composition of a device or devices to be used in a method for the stimulation of human and animal tissue, allowing for the reduction of inflammation and edema to joints, tissue and nerve bundles associated with trauma. This device consists of the implementation of light-emitting diode technologies such as modulated light frequencies and wavelengths but not limited to this technology. In addition, the design incorporates custom software programming and engineering allowing for diagnostic interpretation, biomedical recording and patient statistical/historical medical events in "real time" mode. This will allow for the data to be transmitted via telemetry or "direct connect" to other diagnostic equipment.

PRIOR ART REFERENCES

U.S. Patent Documents

| Patent # | Date | Author |
| --- | --- | --- |
| 4932934 | June 1990 | Dougherty et al. |
| 5161526 | November 1992 | Hellwing et al. |
| 5171749 | December 1992 | Levy et al. |
| 5259380 | November 1993 | Mendes et al. |
| 5282842 | February 1994 | Changaris. |
| 5283255 | February 1994 | Levy et al. |
| 5304167 | April 1994 | Freiberg. |
| 5320618 | June 1994 | Gustafsson |
| 5358503 | October 1994 | Bertwell et al. |
| 5360734 | November 1994 | Chapman et al. |
| 5422362 | June 1995 | Vincent et al. |
| 5707986 | January 1998 | Miller et al. |
| 5993442 | November 1999 | Omori |
| 5944748 | August 1999 | Mager et al. |
| 5951596 | September 1999 | Bellinger |
| 5957960 | September 1999 | Chen et al. |
| 5993442 | November 1999 | Omori |
| 6171331 | January 2001 | Bagraev, et al. |
| 6267779 | July 2001 | Gerdes |
| 6350275 | February 2002 | Vreman, et al. |
| 6393315 | May 2002 | Aprahamian, et al. |
| 20010049609 | November 2001 | Benni et al. |
| 20010045564 | November 2001 | Koike et al. |
| 20020029071 | March 2002 | Whitehurst, Colin |
| 20020077553 | June 2002 | Govari, Assaf; et al. |

Foreign Patent Documents

| Patent | Date | Country ID |
| --- | --- | --- |
| 4113803 | October 1992 | DE. |
| 4112275 | November 1992 | DE. |
| 4129192 | March 1993 | DE. |
| 4707945 | November 1991 | RU. |
| 2014854 | June 1994 | RU. |
| 2018329 | August 1994 | RU. |
| 2033823 | April 1995 | RU. |
| 2032432 | April 1995 | RU. |
| 2034318 | April 1995 | RU. |
| 93003767 | July 1995 | RU. |
| 2043759 | September 1995 | RU. |
| 93015098 | Sepember 1995 | RU. |
| 2045969 | October 1995 | RU. |
| 2049500 | December 1995 | RU. |
| 94019587 | December 1997 | RU. |
| 1781659 | December 1992 | SU. |
| 1810868 | April 1993 | SU. |
| 9321842 | November 1993 | WO. |

OTHER REFERENCES

Medical Association: "The Wonderful Human Machine" (1967)
Gray, J: "Treatment & prevention of injuries in Sports Medicine" Journal of Sports Medicine, Vol. 3 (1975)
Vander, Sherman, Luciano: "Human Physiology—The Mechanisms of Body Functions" (1975)
Anthony C P, Kolthoff N J: "Textbook of Anatomy and Physiology" (1975)
American College of Surgeons: "Therapy to soft tissue wounds" (1977)(1979)
Vander, Sherman, Luciano: "Human Function and Structure" (1979)
Zhou: "Mechanisms of Tumor Necrosis Induced by Photodynamic Therapy" Journal of Photochemistry and Photobiology (1989)
Freitas: "Inflammation and Photodynamic Therapy", Journal of Photochemistry and Photobiology (1991)
Margaron, P: "Photodynamic therapy inhibits cell adhesion without altering integrin expression" (1997)
Hill, R.: "Photodynamic Therapy (PDT) for Antifibrosis . . . " (1995)
American Academy of Orthopedic Surgeons (1999)
American Medical Association: (1999–2001)
Gray H.: "Anatomy of the Human Body" (1918) Revised & Re-Edited, Warren H. Lewis (2001)

STATEMENT REGARDING FEDERALLY SPONSORED RESEARCH

There is NO claim for federal support in research or development of this product.

DESCRIPTION

Background Of Invention

Pathology of Inflammation:

To reduce such pain and suffering as found in joint inflammation and tissue edema, which are associated with the conditions of muscular strain, muscular stress, arthritis, blunt trauma, surgical procedures . . . Common methods have been introduced to the public. This range from the use of external chemicals and ointments, cold and heat treatments to sophisticated physical therapy applied to the area of inflammation in question. The principle behind this action is to stimulate blood flow and circulation to the effected area. Over the past several years, light technology and photosensitizing agents have been used to reduce edema to surrounding tissues during pre and post surgical procedures to sensitive areas such as the eyes.

When the body has been injured either by accident or through medical procedures there is going to be a period of time where inflammation and edema will set into the effected tissue area. This is a natural defense mechanism that is extremely valuable to the body whether it is human or mammal.

To understand this problem in more detail, one must understand the five—(5) common signs of inflammation and the metabolic phases at which they occur. When in the process or reviewing or diagnosing a patient, the following signs are usually identified as follows: (a) swelling (edema), (b) redness or discoloration, (c) radiant heat from the wounded site, (d) pain (tender to the touch) and (e) possible loss of motor or neurological functions to the affected area. In addition, there are three primary metabolic phases which inflammation progresses through and they are usually identified as degenerative, vascular and healing.

Of these three phases, the vascular and healing phases are the most concern to the design and application of this product. Hyper migration and activity of the "Inflammatory Cells" such as neutrophils, macrophages, lymphocytes, and monocytes, occur during changes in blood vessels identified as the vascular phase. From this hyper-activity, the capillary and postcapillary networks become flooded and expand causing hyperemia. Due to this proliferation of the capillaries, redness will present itself in the inflamed tissue. Normally, the blood temperatures in the dermal and epidermal layers of tissue are cooler due external ambient temperatures. Increased blood flow to this damaged area of tissue increases the temperature to ranges that area similar to blood found in the heart or aorta. This effect is the heat or warm feeling that surrounds the wound or injured area.

The physiology of the human body to heal, is directly associated with the aforementioned cells (neutrophils and monocytes). These cells, as a family, are known as leukocytes. As they move along the blood vessel walls looking for fissures or gaps through which they can migrate, leukocytes begin to attack dying or dead cells. This begins a process of releasing a fluid that combines with a serous substance being extrude from the wall of the blood vessel. Later this process helps in the reduction of pathogenic microorganisms to develop into the blood stream. Another cell, known as a platelet, begins the adhesion process to the walls of the damaged vessel. Fibrin fibers simultaneously appear forming a fine mesh and developing a "clot" which pulls the damaged edges of the wound together whether this is an internal tear or external laceration.

Brief Technical Information:

The device or inventions that are to be developed relate to the field of Photochemistry and Photobiology as it applies to inflammation, edema, muscular and neural stimulation of human and mammal skin tissues. As a design, this device may be applied in the field of pharmacotheraputics with the use of photodynamic therapy but not required. Sports Medicine has developed a major need for this type of product for the service of patients, of all age groups, acquiring the need for immediate and/or long-term controlled noninvasive, noncoherent radiant heat therapy specific to the inflammation of joints, tendons and ligaments. Most common needs are associated with arthritis, sprain, strains, tears, blunt trauma and orthopedic surgery of the joint membranes or the loss of damaged cartilage.

Some of the major conditions, syndromes, disease and associated disorders that will benefit from this type of technology are including, but not limited to: Ankylosing Spondylitis (AS), Avascular Necrosis Osteonecrosis), Back Pain, Behcet's Disease, Bursitis and Other Soft Tissue Diseases, Calcium Pyrophosphate Dihydrate, Crystal Deposition Disease (CPPD) (Pseudo Gout), Carpal Tunnel Syndrome, Connective Tissue-Related Diagnoses, Crohn's Disease, Dermatomyositis, Ehlers-Danlos Syndrome (EDS), Fibromyalgia, Giant Cell Arteritis and Polymyalgia Rheumatica Gout, Inflammatory Bowel Disease, Juvenile Arthritis and Related Conditions, Juvenile Dermatomyositis, Juvenile Non-Inflammatory Disorders, Juvenile Psoriatic Arthritis, Juvenile Rheumatoid Arthritis (JRA), Juvenile Scleroderma, Juvenile Spondyloarthropathy Syndromes, Juvenile Systemic Lupus Erythematosus (SLE), Juvenile Vasculitis, Lupus, Lyme Disease, Mixed Connective Tissue Disease (MCTD), Marfan Syndrome, Myofascial Pain, Myositis (Polymyositis, Dermatomyositis), Osteoarthritis, Osteogenesis Imperfecta, Osteonecrosis (Avascular Necrosis Arthritis), Osteoporosis, Paget's Disease, Polyarteritis Nodossa and Wegener's Granulomatosis, Polymyalgia Rheumatica and Giant Cell Arteritis, Polymyositis, Pseudoxanthoma Elasticum (PXE), Psoriatic Arthritis, Raynaud's Phenomenon, Reflex Sympathetic Dystrophy Syndrome, Reactive Arthritis (Reiter's Syndrome), Rheumatoid Arthritis, Sarcoidosis, Scleroderma, Sjogren's Syndrome, Soft Tissue Disease, Still's Disease, Systemic Lupus Erythematosus (Lupus), Tendinitis, and Wegener's Granulomatosis.

The goal is to improve the outcome of the treatment by shortening the period of edema and tenderness and muscular atrophy in the local area and surrounding tissue.

Prior Identified Art:

A method of treating diabetic angiopathy of inferior limbs (Russian Patent No. C1, 2049500, Dec. 10, 1995) is known that implies an internal irradiation of blood with a low-frequency IR emission. A method of treating diabetes mellitus (Russian Patent No. C1 2018329 Aug. 30, 1994) is known that uses a coherent emission to directly irradiate the liquid blood component. The above methods imply a direct effect of an internal irradiation upon the blood. They, however, provide no possibility to affect the physiological processes in tissue cells, or their effects are mediated by a number of uncontrolled factors. Besides, a coherent IR emission used in this case features a lower degree of penetration into tissues, which makes its effect on the tissue structure less organic and, consequently, more rigid.

A device for general local body heating (German Patent No. 4113803, 1992) is known that provides a deep penetration of IR emission into a human body. A rise of tissue temperature that leads to an enhanced necrosis and drying of tissues in the process of their healing, thus promoting a secondary inflammatory process and introducing an additional, however, provide its curing effect risk factor in case of vasodilatation in pathologically changed tissues.

A method of treating skin injuries (Russian Patent No. C1 2032432 Apr. 30, 1995) is known based and the effect produced by a pulsed monochromatized light beam in the red wavelength band. The beam pulse mode, however, is applied in a limited wavelength band as the treated tissues are exposed to light having the wavelength of only 0.6 to 0.69. mu.m at a reduced power density of 5 to 10 mW/cm-.sup.2. Thus, it cannot produce a curing effect for the whole class of diseases accompanied by metabolic disorders.

A multi-wavelength medical laser (U.S. Pat. No. 5,304, 167 Apr. 19, 1994) is known that generates a first beam of pulsed electromagnetic energy and a second beam of electromagnetic energy having its wavelength in a visible portion of the optical spectrum, with both of them affecting the tissues simultaneously. This reference, however, discloses that the laser's wave energy is used for surgery rather than therapy.

An apparatus for thermal stimulation (Russian Patent No. 2045969 C1, Oct. 20, (1995) is known that affects tissues by IR emission in order to stimulate tissue processes. However, the stimulation used for the purpose is thermal.

A method of stimulating biologically active points (Russian Patent No. 93003767 A, Jul. 27, 1995) is known that stimulates body processes through use of IR-range wavelengths that feature a better penetration through the skin. However, the irradiation waveband ranges from 0.8 to 3.mu.m with its source located over the biologically active points affecting the entire body functions, rather than over the organ that controls the course of disease, thus leaving the disease out of consideration.

A method for treating the bleeding of hemophiliacs (U.S. Pat. No. 5,161,526 Nov. 10, 1992) is known based on biostimulation of affected regions of muscles and joints with a beam of light. This method, however, is applied only to stop bleeding and to increase blood coagulability through use of wavelengths ranging from 5.0 to 1.1 mu.m that are not effective for curing the whole set of medical indications typical to the entire class of diseases in question.

A method of affecting biological objects (Russian Patent No. 93015098 A, Sep. 10, 1995) is known that uses modulated pulses of energy, for instance IR energy, to optimize functioning of the biological object energy system and to affect the region of a sore organ. This method, however, does not imply affecting metabolic, regenerative, and enzymatic processes in tissues by treating disorders in tissue capillary circulation, vascular circulation, flow of lymph, as well as treating deceleration of blood flow and oxidation-reduction processes that cause functional, anatomic, and morphological changes in the structure of tissues of all kinds. Besides, the produced effects provide no increase to the curing efficiency compared to the optimum curing effect for diseases caused by disorders of metabolic, regenerative and enzymatic processes in tissues.

The closest to the suggested method of treatment is a method of treating gastric and duodenal ulcers (Russian Patent No. 94019587 A, 1997), implying a 1 to 20 minute transcutaneous irradiation of the affected region of mucosa with IR emission having the power density of 50 to 300 mW/cm.sup.2. However, the efficiency of this method is rather low, since the irradiation is performed through the skin site located directly over the affected region of mucosa and is unable to produce an optimum effect on metabolic, enzymatic, and regenerative processes in tissues. The emission has the wavelength from 7 to 25 mu.m. The given method of treatment provides a curing effect after a large number of irradiation sessions, however, complications are observed in the form of tissue necrosis and edema that decrease the efficiency of treatment by lowering the level of effects on tissues' regenerative, enzymatic, and metabolic processes. This is caused by the fact that the shallow penetration of the emission is unable to activate all the potentials of tissue structures across their entire thickness. Besides, activation and optimization of processes in tissues is also not equally effective for different types of tissues, different locations of affected tissues (deep or shallow), and different types of diseases. This increases the risk of relapses and complications, and decelerates the tissue healing process, since certain undesirable effects like necrosis, keloid cicatrices, and tissue edema have sufficient time to evolve.

A selective polarizing laser mirror (Russian Patent No. 2034318 C1, Apr. 30, 1995) is known with a multi-layer dielectric coat applied onto an optical substrate. The mirror polarizes the emission. The latter, however, is generated by another source; hence, the given device cannot control its polarization parameters.

A method of filtering optical emission (SU No. 1810868 C1, Apr. 23, 1993) is known based on a linear polarization of light. The method makes it possible to cut off a long-wave portion of the emission and to continuously vary the limiting passband frequency. However, it cannot linearly polarize a specific wavelength of the emission that varies in accordance with the task.

A device for treatment of undesired skin disfigurements (U.S. Pat. No. 5,320,618 Jun. 14, 1994) is known that emits a pulsating light beam. However, the light wavelength transformer used in the device does not respond to wavelength variations and cannot provide an optimum curing effect by combining a specific wavelength of the emission with a certain magnitude of its pulsation.

High energy light emitting diodes (LED's) for photodynamic therapy (PCT Patent No. 93/21842 A1, 1993) are known. The device and the method suggested for activating the healing processes by photodynamic therapy utilize the emission of powerful LED's in a certain pre-selected portion of the optical spectrum. However, a complex feedback circuit needed to monitor the light parameters makes it impossible to adjust the device to a specific type of disease.

A polarizing grating (SU No. 1781659 C1, Dec. 15, 1992) is known that polarizes light in a broad waveband from 1 to 100.mu.m. However, it provides for no variations of emission parameters required for treating a specific type of disease, since no wavelength selection within the preset band is envisaged. An apparatus for bioenergetic therapy (Russian Patent No. 2043759 C1, Sep. 20, 1995) is known consisting of a pulse generator and an IR generator. However, it cannot provide the required combinations of a specific wavelength of the emission with certain pulse parameters through a direct control over the light emitter to obtain an optimum curing effect for a specific disease.

An irradiating device (German Patent No. 4129192 A1, March 1993) is known that passes the varying portion of the emission through by means of a frequency-selective partially transparent glass. In other words, a spectrum, initially containing parasitic (harmful) components, is emitted and then corrected by a special unit.

An irradiating device (German Patent No. 4112275 A1, 1992) is known in which special spectrum dividers with a diachronic coat divide the spectrum. The device permits to emit a spectrum with preset characteristics, though provides no spectrum variation in combination with and depending upon the length, polarization, and modulation of the wave.

A method and a device for inducing tanning by pulsating light (U.S. Pat. No. 5,282,842, Feb. 1, 1994) are known. However, the device emitter is not included into the circuit designed for varying the pulse cycles, thus the device itself cannot be adjusted to a specific type of disease.

A light therapy system (U.S. Pat. No. 5,259,380 Nov. 9, 1993) is known based on LED's that emit a narrow-band noncoherent light with a central wavelength. The LED's are grouped into diode banks controlled by a device that generates a difference of potentials and a unit that forms a voltage with preset characteristics. However, selection of required emission parameters is performed by the entire system, rather than through use of emitter properties.

A light therapy device (Russian Patent No. 2014854 C1, Jun. 30, 1994) is known that provides a curing effect using a periodic pulsed IR beam of controlled intensity. Metal halogen lamps that have a certain filling and provide control over the intensity and spectral composition of the emitted light, though being unable to provide its linear polarization and ensure generate the emission an optimum combination of the wavelength, modulation, and polarization required for treating a specific disease.

Light therapy devices comprising light emitters and a control system (Russian Patent No. 2014854 C1, Sep. 20, 1994; and Russian Patent No. 2033823 A1, Sep. 20, 1995) are the closest by their engineering solution to the proposed device. Their emitters are calibrated depending on the requirements to the emitted flux density, and the process of controlling the flux parameters depends on the program of therapy. However, the control over the flux parameters is secured by changing the location of the emitter relative to the pathology focus or by changing the emitters themselves, which prevents selection of an optimum combination of emission characteristics to obtain the maximum curing effect for a specific disease.

The method for treating inflammatory processes and uncomplicated ulcerations of gastric and duodenal mucosa (Russian Patent No. 4707945 A1, Nov. 26, 1991) is the closest by its technical essence to the suggested method of treating pathological tissues. It envisages a possibility of simultaneous treatment of both the surface layers of mucosa and deeper layers of the organ walls with a partial absorption of the irradiation by the tissues located between these layers. However, the applied spectral band can be varied only by combining the powers supplied to the emitter, for instance to a set of halogen lamps, or by changing the distance from the distal end of an endoscope to the irradiated tissue surface. The method does not allow combining polarization and modulation together with power and wavelength variation to obtain an optimum combination of emission parameters for treating a specific disease.

DETAILED DESCRIPTION OF THE INVENTION

The Joint/Tissue Inflammation Therapy and Monitoring Device or "JIT-Mon" is made of a neoprene elastic material like that found in wetsuits. Sizing of the device will be made with Velcro type straps allowing for an easy and comfortable fit. Each JIT-Mon has strategically located Light Emitting Diodes (LED's) with calibrating wavelengths and modulated light frequencies to allow for controlled heat/energy and muscular therapy to an area of inflammation. Additional monitoring devices, using optical fiber, photodetector and photoresin technologies, are integrated into the JIT-Mon device and are supported with customized software and hardware. This information and technology allows a physician or therapist to monitor and record vital information such as blood flow in the area, skin temperature and moisture to an external-monitoring device.

By surrounding the injured and inflamed areas with an elastic fitted device, which applies controlled heat/energy using Light Emitting Diodes, (LED's) at specific modulated light frequencies and wavelengths will enhance the recovery process. Understanding of the anatomy and physiology of the body and its process to healing, helps the physician or therapist apply proper heat/energy where needed. This improves blood flow and enhances the natural release of cells and chemicals to improve the overall recovery of the patient. Each device is made to fit the areas of the joints and skeletal system especially the neck, thoracic, knee, elbow and tarsal and carpal appendages. The device has the ability to integrate optical fiber and photoresin technology, solid state detectors, sonic/ultrasonic transducers or other high level inputs.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 is an enlarged sectional view taken from FIG. 1 of the multi-layered LED's of the Phototherapy Device showing the positions of different colored LED's.

DETAILED DESCRIPTION OF INVENTION

The numeric designations as set forth in FIGS. 1–4 are described in the following manner.

Figure 1:
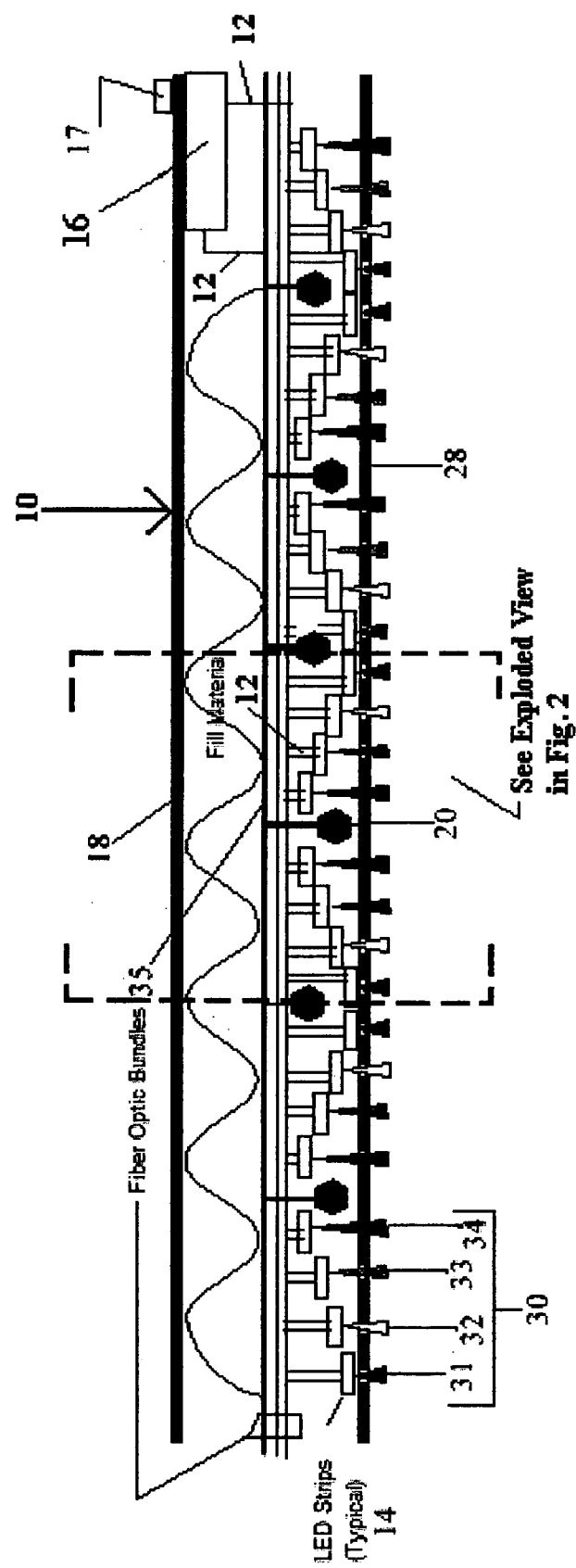
FIG. 1 is a detailed cross-section of the Phototherapy Device with the colors of LED's being identified.

FIG. 1 is a detailed cross-section of the Phototherapy Device (10) having LED strips (14) with a plurality of LED's (30), with wavelengths ranging from 350 nm–1000+ nm positioned toward the skin tissue. The plurality of LED's is identified as to color (31, 32, 33, 34 respectively), fiber optic strips (12) for therapy, biomedical feedback and control of the Phototherapy Device (10);

each LED strip (14) is fixed in layers with a first layer near contact with the skin and with other layers at a distance that is farther from the skin, and with the distance being wavelength dependent;

data processing circuit (16) consisting of a VDC Power Supply, Central Processing Unit (CPU), fiber optic strips (12) integrated with photon detector (20) and an electronic communications circuit (17) for biomedical feedback and control of the Phototherapy Device (10).

To be more specific in FIG. 1 the data processing circuit with 3.5–5.0 VDC CPU, LED/fiber optic connectivity integrated with PMT technology, telemetry, CCD integration, A/D I.O. using USB connections is identified as (16) with further identification of components being;

the exterior surface material (18) and internal surface material (28) are of thin neoprene or other non-allergenic materials;

laser diodes with photodetector technology and biofeedback sensors integrated with PMT technology (20) and fiber optic bundles are identified as (35).

FIG. 2 illustrates an enlarged Cross-Section View, taken from the brackets of FIG. 1 to more clearly identify the multiple layered configuration of LED strips (14), fiber optic bundle (35) for data, electrical and communications throughput;

each LED strip (14) is identified with a color of the LED that is individually numbered as (31, 32, 33 and 34); a photon detector (20) is also identified allowing for biomedical feedback, data analysis and device control.

Figure 3A:
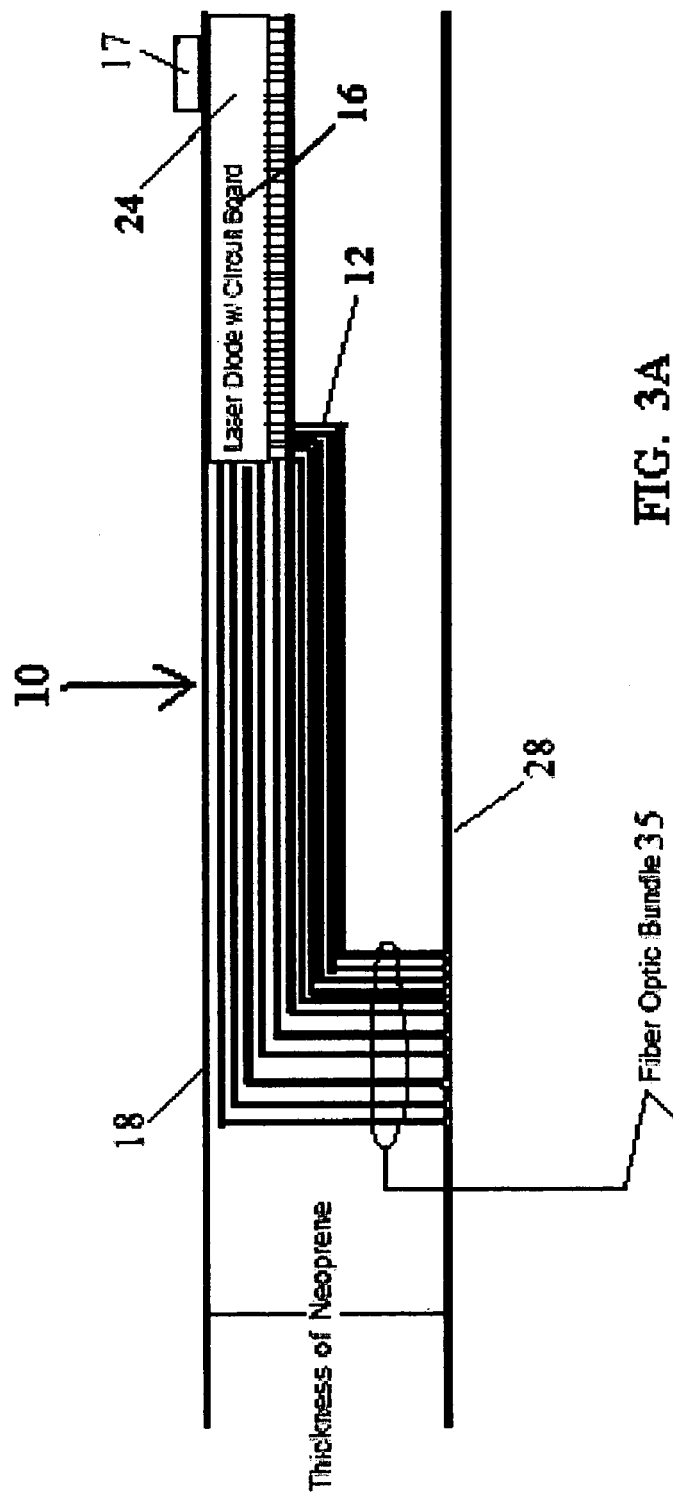
FIGS. 3A–3B is a cross-section of Fiber Optic Bundle attached to a Laser Diode and Circuit Board.
Figure 3B:
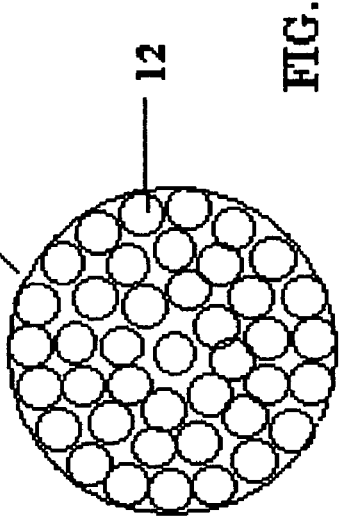

In FIG. 3A an Exploded Cross-Section of the Phototherapy Device (10) shows the fiber optic bundle (35) and single fiber optic strip (12) integrated with the laser diode with circuit board (24) and data processing circuit (16) which integrates with the electronic communications circuit (17), the fiber optic bundle (35) delivers light to the subject site and collects data from the site;

FIG. 3B shows an Exploded Cross-Section of a fiber optic bundle (35) and single fiber optic strip (12).

Figure 4:
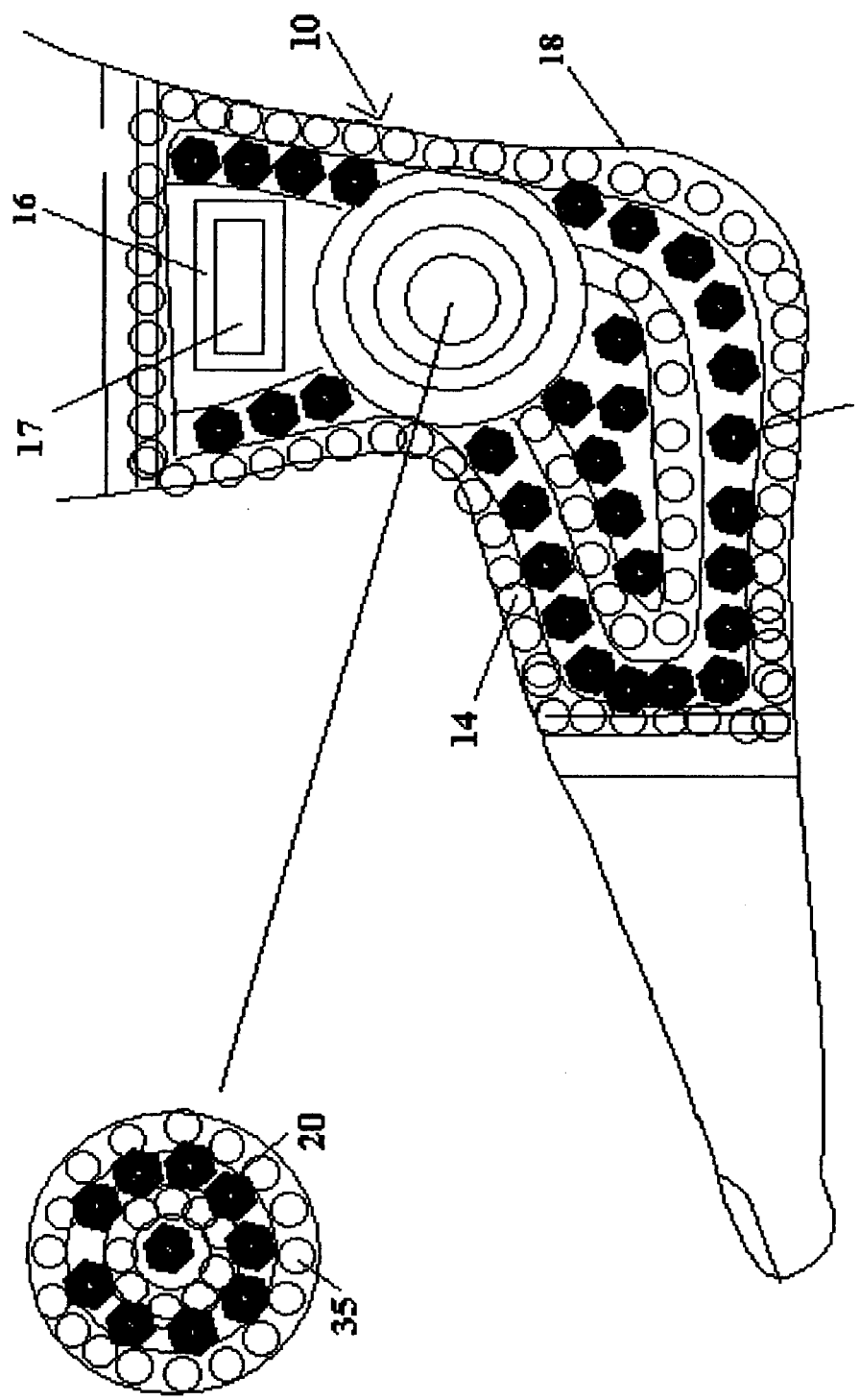
FIG. 4 illustrates the Phototherapy Device as applied to a human ankle.

FIG. 4 is a perspective view of a completed Phototherapy Device (10) as applied to and surrounding a human ankle.

The Phototherapy Device (10) is configured with LED strips (14) and photon detectors (20), data processing circuit (16) and electronic communication circuitry (17).

Enlarged away from the Phototherapy Device (10), in FIG. 4, is a figure illustrating the interface of the fiber optic bundles (35) and photon detectors (20) as they are placed surrounding the protruding bone of the ankle.

Attention is drawn to the fact that in FIGS. 1 and 2, LED's strips (14) with discrete spectra within ranges 350 nm–1000+ nm (31, 32, 33 and 34 respectively) are oriented toward the skin tissue and are identified as grouping (30). Note that the original drawings accompanying this specification were filed in color which identified the LED's as to color. The instant drawings, FIGS. 1 and 2 identify the color of the originally filed LED's by number. These numbers identify color to denote the colors of various wavelengths of LEDs. In drawings originally submitted with the specification, the LED's were presented in color with infrared being furthest from the skin and ultraviolet closest to the skin.

Specifically in FIG. 2, the LED strips (14) ranging 350 nm–1000+ nm are identified in grouping (30) have been redrawn for black and white reproduction and have been identified as 31=color 1 (blue), 32=color 2 (yellow), 33=color 3 (orange) and 34=color 4 (red).

As understood by those skilled in the art, the following abbreviations used herein are defined as follows:

PMT Technology is defined as meaning Photomultiplier Tube Technology.

Spread Spectrum Technology is a term understood by those skilled in the art and is defined in an article in the IEEE Spectrum of August 1990 entitled "Spread Spectrum Goes Commercial" by Donald L. Schilling. This expression is well understood in the art.

Specific sensory devices are well known in the art and are commercially available. They are sensors which detect a specific body condition. They are defined in detail in a publication entitled "Sensors in Biomedical Applications: Fundamentals, Technology and Applications" by Gabor Harsdnyi, Copyright 1999/2000 Culinary and Hospitality Industry Publications Services.

VDC Technology is defined as meaning Voltage Direct Current.

The herein disclosed invention involves a phototherapy device for treating damaged tissue and reducing inflammation and edema both internal and external to joints, muscles, nerves and skin tissues of the subject (human or animal) comprising of:

an elastic, portable device configured to be worn in contact with the skin and surrounding the area or areas to be treated over short and long periods of time; whereas the construction of the device is configured with multiple layers of LED's or laser diodes and fiber optics distributed in a range consisting of near contact with the skin to a few centimeters from the skin tissue; with orientation toward the subject; and having integrated low voltage power; electronic memory and communications via analog/digital connection or telemetric medical sensor; allowing for independent control of tissue temperature and modulation frequencies allowing for varied pulse rates and durations and wavelengths of the LED's or laser diodes. The device is constructed of multiple layer technology integrating the light emitting diodes (LED's) and laser diodes, and fiber optics, and wherein the fiber optics are fiber optic strands and fiber optic bundles.

The device is designed with LED's or Laser Diodes having discrete wavelengths within ranges of 350 nm to 1000+nm. The LED's or Laser Diode wavelength range of 350 nm to 1000+ nm are introduced to the skin tissues allowing for muscular and/or neural stimulation under low light conditions. The device has modulated frequencies allowing for varied pulse rates and durations ranging from less than (<) 1 Hz to less than (<) 1 GHz which will be introduced to the skin tissues allowing for muscular and/or neural stimulation under low light conditions. The device has controlled penetrating light wavelengths and modulated frequencies allowing for varied pulse rates and durations of the light using light-emitting diodes and fiber optics to control heat/energy and duration directly to the injured site.

The device is designed with insulated low voltage being produced by VDC Technology.

The device incorporates a micro circuit board containing an Electronic Erasable Programming Read Only Memory (EEPROM) chip, Central Processing Unit (CPU), CCD Integration, Laser Photo Diodes, Photomultiplier Tube Technology (PMT) biometrics sensory devices and a digital input/output device.

The device incorporates a telemetric monitoring transceiver configured for Spread Spectrum Technology in bandwidths ranging in 2.0+Ghz or others approved by the FCC.

In the device light-emitting diodes and also laser diodes are integrated into the device using wavelengths within ranges of 350 nm to 1000+nm and modulated frequencies allowing for varied pulse rates and durations from less than (<) 1 Hz to less than (<) 1 GHz.

The device has a telemetric medical sensor integrated into the device allowing for physiological monitoring of the patient and for the ability of adjusting the wavelength and modulated frequencies of the LED's or laser diodes.

The device is configured with LED's in multiple layers consisting from depths of contact with the skin and continuing to 3.5 cm or more. That is, a first layer of LED's will be in near contact with the skin with other layers configured at a distance that is farther from the skin surface and up to 3.5 cm or more from the skin.

The device is configured with arrayable holding devices in single, bi-layer, tri-layer and quad-layer configurations allowing for the multiple layers of LED's to be connected to fiber optic cabling encapsulating the skin tissues at multiple points.

The device is designed and configured for the technology of evanescent waves in the wavelengths of Ultra Violet including Blue, Green, Yellow and Red to Near-infrared.

The device is provided with biometrics sensors to monitor induced heat/energy, blood flow, baseline temperatures, oxygenated blood and circulation.

The device is designed to be used with a photosensitizing agent.

The device is provided with a reflective film to provide filtering or polarization characteristics for the light.

The device has software designed and compiled to integrate to the micro circuit board, CCD Technology and EEPROM.

The invention claimed is:

1. A phototherapy device comprising: an elastic, portable device configured to be worn surrounding an area or areas to be treated; the device having integrated low voltage power; electronic memory, medical sensor and communications; multiple LED's or laser diodes configured in multiple layers wherein said multiple layers being in a range of near contact with the skin and continuing to a distance further from the skin and wherein the LED'S or laser diodes are independently controllable using electronics and fiber optics via a microprocessor, said control including modulation, pulse rates and pulse duration.

2. The phototherapy device of claim 1 wherein the multiple layers of LED's or laser diodes range from near contact with the skin to a few centimeters from the skin.

3. The device of claim 1 wherein the device is constructed of multiple layer technology integrating the light emitting diodes (LED's), or laser diodes with the fiber optics, and wherein the fiber optics are fiber optic strands and fiber optic bundles being connected to an integrated circuit to provide data and device control to integrated circuits for control of the LED's and laser diodes.

4. The device of claim 1 wherein the device is designed with LED's or Laser Diodes having discrete wavelengths within ranges of 350 nm to 1000+nm.

5. The device of claim 1 wherein the light generated by LED's or Laser Diodes at modulated light frequencies allowing for varied pulse rate and durations ranging from less than (<) 1 Hz to less than (<) 1 GHz which is introduced to the subject allowing for muscular and or neural stimulation under low light conditions.

6. The device of claim 1, wherein the device is configured with LED's in multiple layers consisting from depths of contact near the skin and continuing to a distance that is farther from the skin and up to 3.5 cm or more.

7. The device of claim 1, wherein the device has configured therewith arrayable holding devices in single, double-layer, tri-layer and quad-layer configurations allowing for plurality of LED's or laser diodes to be connected to the fiber optics in contact with the skin of the subject at multiple points.

8. The device of claim 1, wherein the device is designed and configured for the technology of evanescent waves in the wavelength of Ultraviolet, Blue, Green, Yellow and Red to Near-infrared.

\* \* \* \* \*